(12) United States Patent
Tegg et al.

(10) Patent No.: US 10,070,927 B2
(45) Date of Patent: Sep. 11, 2018

(54) SENSOR ASSEMBLY TETHERED WITHIN CATHETER WALL

(71) Applicant: St. Jude Medical, Atrial Fibrillation Division, Inc., St. Paul, MN (US)

(72) Inventors: Troy T. Tegg, Elk River, MN (US); Brian M. Monahan, Elk River, MN (US); Salome A. Gonzalez, Maple Grove, MN (US); James V. Kauphusman, Champlin, MN (US); Sacha C. Hall, Westborough, MA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 921 days.

(21) Appl. No.: 14/519,313

(22) Filed: Oct. 21, 2014

(65) Prior Publication Data

US 2015/0107766 A1    Apr. 23, 2015

Related U.S. Application Data

(63) Continuation of application No. 13/098,969, filed on May 2, 2011, now Pat. No. 8,880,147.

(51) Int. Cl.
*A61M 25/00* (2006.01)
*A61B 19/00* (2006.01)
(Continued)

(52) U.S. Cl.
CPC .......... *A61B 19/5244* (2013.01); *A61B 5/062* (2013.01); *A61B 5/063* (2013.01);
(Continued)

(58) Field of Classification Search
CPC ......... A61B 34/20; A61B 5/062; A61B 5/063; A61M 25/001; A61M 25/0127; A61M 2025/0062; A61M 25/004; A61M 25/0012
See application file for complete search history.

(56) References Cited

U.S. PATENT DOCUMENTS 6,203,493 B1    3/2001    Ben-Haim
6,233,476 B1    5/2001    Strommer
(Continued)

FOREIGN PATENT DOCUMENTS

JP    H11-267095    10/1999
JP    2002514947    5/2002
(Continued)

OTHER PUBLICATIONS

An International Search Report for PCT Application No. PCT/US2012/023353, dated Feb. 1, 2013, 3 pgs.
(Continued)

*Primary Examiner* — Christopher T Schatz
(74) *Attorney, Agent, or Firm* — Dykema Gossett PLLC

(57) ABSTRACT

A distal tip assembly for an elongate medical device having an axis comprises a shaft having a proximal end portion, a distal end portion, a wall, and a central lumen extending axially between said proximal end portion and said distal end portion. The distal tip assembly further comprises a position sensor disposed in an outer sleeve such that the sensor can shift relative to the sleeve. The sleeve is disposed at least in part in the wall and is substantially fixed thereto.

15 Claims, 9 Drawing Sheets

(51) Int. Cl.
*A61B 5/06* (2006.01)
*A61M 25/01* (2006.01)
*A61B 34/20* (2016.01)
*A61B 17/00* (2006.01)

(52) U.S. Cl.
CPC .............. *A61B 5/065* (2013.01); *A61B 34/20* (2016.02); *A61M 25/001* (2013.01); *A61M 25/0012* (2013.01); *A61M 25/0127* (2013.01); *A61B 5/068* (2013.01); *A61B 2017/00526* (2013.01); *A61B 2017/00867* (2013.01); *A61B 2034/2051* (2016.02); *A61B 2562/0223* (2013.01); *A61M 2025/0166* (2013.01); *A61M 2207/00* (2013.01); *Y10T 156/10* (2015.01)

(56) References Cited

U.S. PATENT DOCUMENTS

| | | | |
|---|---|---|---|
| 6,690,963 | B2 | 2/2004 | Ben-Haim et al. |
| 7,197,354 | B2 | 3/2007 | Sobe |
| 7,245,955 | B2 | 7/2007 | Rashidi |
| 7,263,397 | B2 | 8/2007 | Hauck |
| 7,386,339 | B2 | 6/2008 | Strommer et al. |
| 7,536,218 | B2 | 5/2009 | Govari |
| 7,706,891 | B2 | 4/2010 | Hastings |
| 7,774,051 | B2 | 8/2010 | Voth |
| 7,789,877 | B2 | 9/2010 | Vanney |
| 7,819,866 | B2 | 10/2010 | Bednarek |
| 7,848,789 | B2 | 12/2010 | Govari |
| 7,850,642 | B2 | 12/2010 | Moll |
| 8,052,636 | B2 | 11/2011 | Moll |
| 9,057,628 | B2 | 6/2015 | Drespling et al. |
| 2003/0100895 | A1 | 5/2003 | Simpson |
| 2004/0034348 | A1 | 2/2004 | Rashidi |
| 2004/0186377 | A1* | 9/2004 | Zhong ................. A61M 25/00 600/431 |
| 2005/0033135 | A1 | 2/2005 | Govari |
| 2006/0241366 | A1 | 10/2006 | Falwell |
| 2006/0293643 | A1 | 12/2006 | Wallace |
| 2008/0094226 | A1 | 4/2008 | O'Shea et al. |
| 2008/0161774 | A1 | 7/2008 | Hasting |
| 2009/0131910 | A1 | 5/2009 | Webler |
| 2010/0324412 | A1 | 12/2010 | Govari et al. |
| 2012/0071895 | A1 | 3/2012 | Stahler |
| 2012/0126796 | A1 | 5/2012 | Drespling |
| 2012/0172716 | A1* | 7/2012 | Sela ........................ A61B 5/06 600/424 |

FOREIGN PATENT DOCUMENTS

| | | |
|---|---|---|
| JP | 2006504473 | 2/2006 |
| JP | 2011005251 | 1/2011 |
| WO | 1997/029679 | 8/1997 |
| WO | 2004/039273 | 5/2004 |
| WO | 2009055651 | 4/2009 |
| WO | 2010085374 | 7/2010 |
| WO | 2011012511 | 2/2011 |

OTHER PUBLICATIONS

A Supplementary European Search Report for EP Application No. 12779319, dated Sep. 25, 2014. 3 pgs.

* cited by examiner

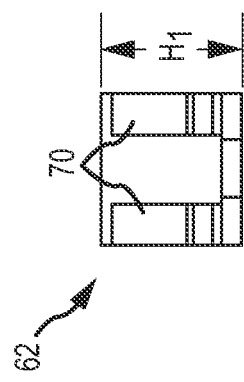
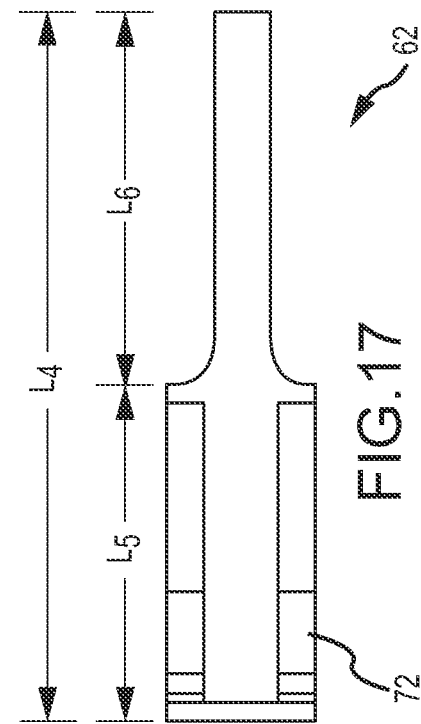
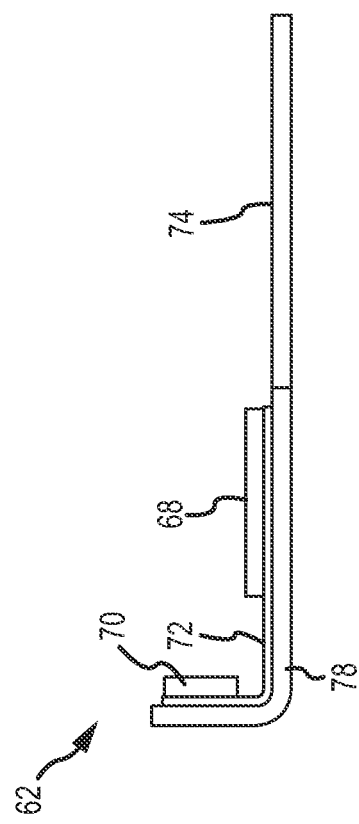

SENSOR ASSEMBLY TETHERED WITHIN CATHETER WALL

CROSS-REFERENCE TO RELATED APPLICATIONS

This application is a continuation of U.S. application Ser. No. 13/098,969, filed 2 May 2011, now pending, which is hereby incorporated by reference as though fully set forth herein.

BACKGROUND OF THE INVENTION a. Field of the Invention

The present disclosure relates to a family of positioning sensors for a medical device and a method for mounting an electromagnetic positioning sensor on a medical device to avoid potential damage due to compression and tension forces and the like.

b. Background Art

Various diagnostic and therapeutic procedures in or on the body of a patient, such as in the heart or elsewhere in the circulatory system, can be performed or facilitated by inserting an electrophysiology (EP) catheter into a body lumen and thereafter navigating the diagnostic or therapeutic EP catheter to the target anatomical site. The EP catheter can include one or more electrodes to be used for therapeutic (e.g., ablation), diagnostic, or other purposes.

For certain procedures, it is desirable for the distal end of an EP catheter to have a particular curve or shape or to include uni- or bi-directional deflection elements, for example. For example, some ablation or mapping procedures on certain portions of the heart or the vasculature around the heart, such as the superior pulmonary vein, can be simplified through the use of an EP catheter having a lariat or spiral shape on its distal end. In order to achieve the desired shape, an EP catheter can incorporate one or more shape wires that can be preformed to the desired shape, deformed (e.g., via loading) to guide the catheter to the target anatomical site, then unloaded such that the shape wire—and thus the catheter—returns to the preformed desired shape.

It is also known to configure straight EP catheters (i.e., without shape wires) to include one or more electromagnetic field (position) sensors for navigating the catheter to the target anatomical site. While enabling sensor-based navigation functionality, a straight EP catheter as described above does not have the same applicability to certain EP procedures as does a shaped EP catheter.

There is therefore a need for a catheter that incorporates a shape wire and one or more electromagnetic position sensors that minimizes or eliminates one or more of the problems set forth above.

BRIEF SUMMARY OF THE INVENTION

This disclosure is directed to an elongate medical device configured for use with a positioning system (i.e., the device includes at least one position sensor, such as an impedance-sensing electrode, a metallic/magnetically-responsive coil, and/or an acoustically-responsive element or the like). A distal tip assembly for an exemplary elongate medical device having an axis includes a shaft having a proximal end portion, a distal end portion, a wall, and a central lumen extending axially between the proximal end portion and the distal end portion. The assembly further includes one of an electromagnetic position sensor, an impedance-sensing electrode, and an acoustically-responsive element disposed in an outer sleeve and/or coupled to a stress-reduction flex circuit or other member. The mechanical stress imparted to the sensor is reduced because the sleeve substantially separates the sensor from the wall, so the sensor can potentially shift relative to the sleeve, the wall, or any anchoring location therefor. The sleeve is disposed, at least in part, in the wall and is fixed thereto in a stress-relieving configuration. In an embodiment, the assembly is incorporated into a device that also includes a shape wire for providing a desired preformed shape. The sensor-in-sleeve arrangement described above allows the sensor to move with respect to the shape wire or other deflection mechanism when assembled for use in a medical procedure. This permitted movement avoids damage to the sensor that can otherwise occur had the sensor been rigidly fixed in the wall.

A method of fabricating a distal tip assembly for the exemplary device includes a number of steps that include providing a first shaft layer and placing, at a distal end portion of the elongate medical device, a position sensor assembly on the first shaft layer. The position sensor assembly includes a tubular core, an electrically-conductive coil wound on said core, and an outer sleeve surrounding the core and the coil. The method further includes applying a second shaft layer radially-outwardly of the position sensor assembly and of the first shaft layer, and subjecting the tip assembly to a reflow lamination process. In the reflow lamination process, the first shaft layer and the second shaft layer bond to an outer surface of the sleeve, and the coil and the core can shift within the sleeve.

These and other benefits, features, and capabilities are provided according to the structures, systems, and methods depicted, described and claimed herein.

BRIEF DESCRIPTION OF THE DRAWINGS

FIGS. 14-17 are various isometric and plan views of an embodiment of a flex circuit according to the disclosure.

DETAILED DESCRIPTION OF THE INVENTION

Figure 1:
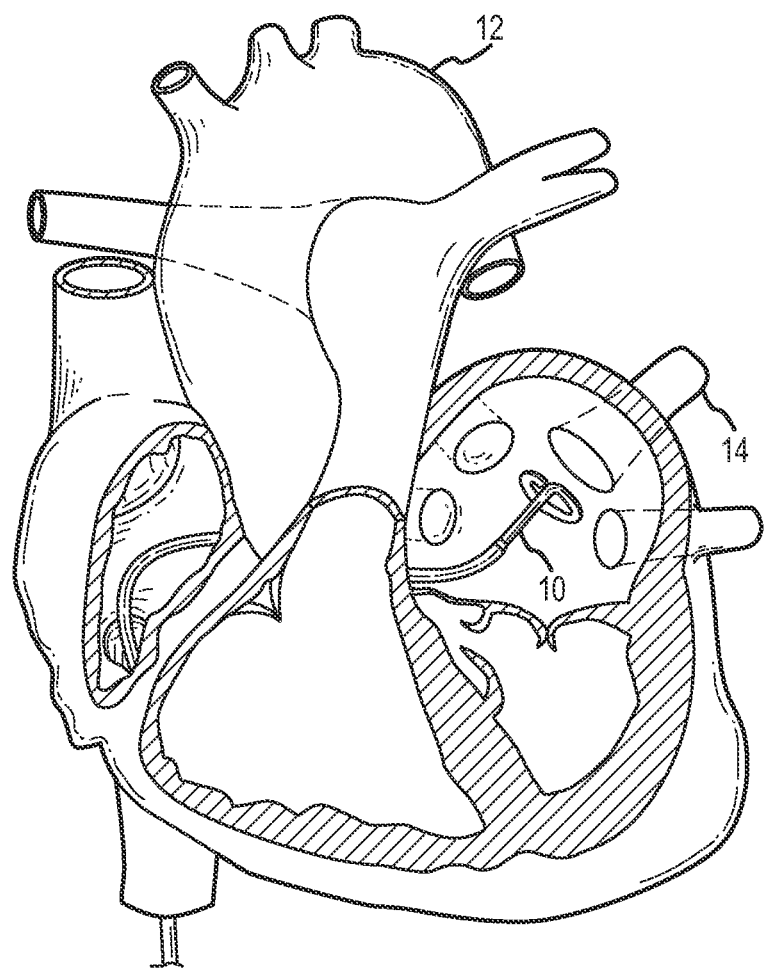
FIG. 1 is a simplified view of a first embodiment of an elongate medical device, with a distal lariat portion, within a human heart.

Referring now to the drawings wherein like reference numerals are used to identify identical components in the various views, FIG. 1 is a simplified view of a first embodiment of an elongate medical device 10. Device 10, shown as a catheter, is disposed in the left atrium of a human heart 12. As depicted, device 10 comprises a spiral electrophysiology (EP) mapping catheter incorporating at least one electromagnetic-, impedance-, or acoustic-based position sensor, though the present invention can also find use with a spiral EP ablation catheter, another EP catheter, or another medical device for which an electromagnetic position sensor would be useful. A spiral mapping catheter, such as catheter 10, can be particularly useful for mapping ingress and egress points of the human heart, such as superior pulmonary vein 14, as well as for other portions of the human vasculature. An EP mapping catheter can be used in the heart and vasculature to collect EP data as described in greater detail in commonly-owned U.S. Pat. No. 7,774,051, entitled "System and Method for Mapping Electrophysiology Information Onto Complex Geometry," which is hereby incorporated by reference in its entirety. Device 10, or another device employing an electromagnetic position sensor and/or EP electrodes, can be used with a variety of navigation and mapping systems such as, for example, an ENSITE VELOCITY system running a version of the ENSITE NavX™ software commercially available from St. Jude Medical, Inc., of St. Paul, Minn. and as also seen generally by reference to U.S. Pat. No. 7,263,397 entitled "Method and Apparatus for Catheter Navigation and Location and Mapping in the Heart" to Hauck et al., owned by the common assignee of the present disclosure, and hereby incorporated by reference in its entirety. Device 10 can also find use with other known technologies for locating/navigating a catheter in space (and for visualization), including for example, the CARTO visualization and location system of Biosense Webster, Inc., (e.g., as exemplified by U.S. Pat. No. 6,690,963 entitled "System for Determining the Location and Orientation of an Invasive Medical Instrument," hereby incorporated by reference in its entirety), the AURORA® system of Northern Digital Inc., a magnetic field based localization system such as the gMPS system based on technology from MediGuide Ltd. of Haifa, Israel and now owned by St. Jude Medical, Inc. (e.g., as exemplified by U.S. Pat. Nos. 7,386,339, 7,197,354 and 6,233,476, all of which are hereby incorporated by reference in their entireties) or a hybrid magnetic field-impedance based system, such as the CARTO 3 visualization and location system of Biosense Webster, Inc. (e.g., as exemplified by U.S. Pat. No. 7,536,218, and 7,848,789 both of which are hereby incorporated by reference in its entirety).

An EP catheter employing one or more shape wires can include one or more electromagnetic position sensors for navigating the catheter to the target anatomical site with one or more of the technologies described above. Assembling electromagnetic coil sensors within the space constraints of a catheter without sacrificing sensitivity presents various design and manufacturing challenges. One such challenge is incorporating a sensor in a portion of a catheter that can be bent by a shape wire in a way that can place stress on the shaft of the catheter and on components disposed within the shaft, such as an electromagnetic sensor.

FIGS. 2-6 are diagrammatic cross-sectional side views of a reflow mandrel assembly in various stages of build-up in a method of manufacture of a distal tip assembly 40 with an electromagnetic position sensor for device 10. It should be understood that although gaps are shown between the several layers of material, such gaps are shown for visual clarity and can or cannot be present in the actual manufacturing process and final product. Elements shown in FIGS. 2-6 are not necessarily to scale. Furthermore, "assembly 40" is used herein to refer both to the distal tip assembly as it is built up and constructed, as well as to the finished distal tip assembly.

Figure 2:
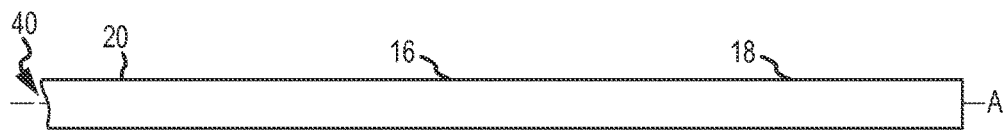
FIGS. 2-6 illustrate a method of fabricating a distal tip assembly for the device shown in FIG. 1.

FIG. 2 shows a mandrel 16 having a central axis "A," a distal end portion 18, and a proximal end portion 20. Mandrel 16 can be circular in radial cross-section and have a desired length in view of the elongate medical device or portion thereof to be manufactured. Mandrel 16 can have grooves to facilitate the application and removal of materials, or can be smooth.

Figure 3:

As shown in FIG. 3, a first segment $22_1$ of a first shaft layer 22 can first be placed over mandrel 16. First shaft layer 22 can consist of multiple segments $22_1$, $22_2$, $22_3$ (best shown in FIGS. 5 and 6). First shaft layer 22 can be any suitable tubing material known in the art of medical instruments, such as engineered nylon resins and plastics, including but not limited an elastomer commercially available under the trade designation PEBAX® from Arkema, Inc. of a suitable durometer, melting temperature and/or other characteristics. First segment $22_1$ can have an axial length configured to be substantially equal to the length of a sensor or sensor assembly to be incorporated into distal tip assembly 40.

Figure 4:
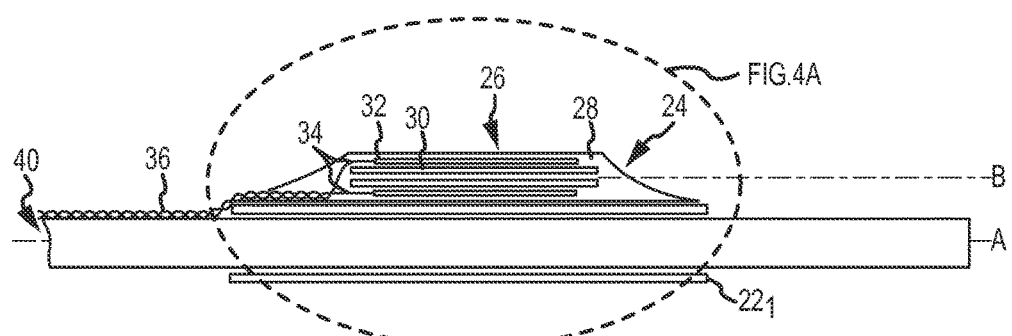
Figure 4A:
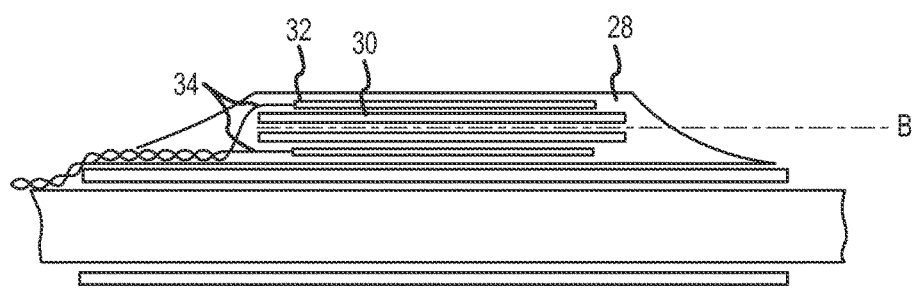

A position sensor assembly 24 can be provided for position sensing and device navigation in the finished device 10. As shown in FIGS. 4 and 4A, position sensor assembly 24 can be placed on top of first shaft layer 22. In the illustrated first embodiment, sensor assembly 24 is placed on first segment $22_1$. Sensor assembly 24 can include a sensor 26 within an outer protection sleeve, or tube, 28. Sensor 26 can be an electromagnetic field-detecting coil-type sensor, as shown. Electromagnetic coil sensor 26 can comprise a tubular core 30 and an electrically-conductive coil 32 wound around core 30. Core 30 can be a hollow tube made of a polymer with a relatively high melting point, such as polyimide, so as to maintain shape during a high-temperature reflow lamination process, such as seen by reference to co-pending U.S. patent application Ser. No. 12/982,120, entitled "Electromagnetic Coil Sensor for a Medical Device," hereby incorporated by reference in its entirety. Core 30 can also be solid, rather than hollow (shown in FIG. 13). Core 30 can have a central axis "B" that is substantially parallel with, but radially offset from, mandrel central axis "A." Because axis "A" can also be the central axis of device 10 and distal tip assembly 40, sensor axis "B" can be substantially parallel with, but radially offset from, axis "A" of device 10. Coil 32 can be made of electrically-conductive wire wrapped around core 30. Coil 32 is not limited in number or pitch of windings, or type of wire, but instead can be tailored to suit a particular application of sensor 26. Coil 32 can have one or more free leads 34 at its proximal end for connection to one or more wires 36. Wiring 36 can be coupled to coil leads 34 and extend towards the proximal end of device 10 to provide electrical connection with a positioning system, navigation system, or other system. One or more wires 36 can be in the form of a twisted-pair (TP) cable as shown in FIGS. 4-6, can be a coaxial cable, or can be another electrical signal or power cable known in the art.

Outer sleeve 28 can be provided to prevent sensor 26 from being directly embedded in the shaft of finished device 10. Sleeve 28 can extend both distally and proximally beyond the axial length of sensor 26 (i.e., both core 30 and coil 32)

and can fully circumferentially surround sensor 26 (again, both core 30 and coil 32). Sleeve 28 can have a length that is substantially the same as the length of first shaft layer segment $22_1$. Sleeve 28 can be made of expanded polytetrafluoroethylene (ePTFE), polytetrafluoroethylene (PTFE), polyimide, fluorinated ethylene propylene (FEP), polyether ether ketone (PEEK), or other material interposed between first shaft layer 22 and other shaft layers and sensor 26, which prevents such shaft layers from encapsulating and thus rigidly fixing sensor 26 therein during a high-temperature reflow lamination process. Sleeve 28 can be circumferentially sealed and can be sealed at its distal end, but can have a hole at its proximal end for wiring 36 or sensor coil leads 34 to extend into or out of sleeve 28.

Figure 5:
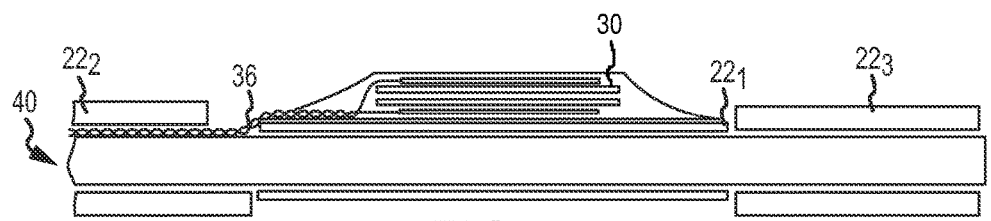
Figure 6:
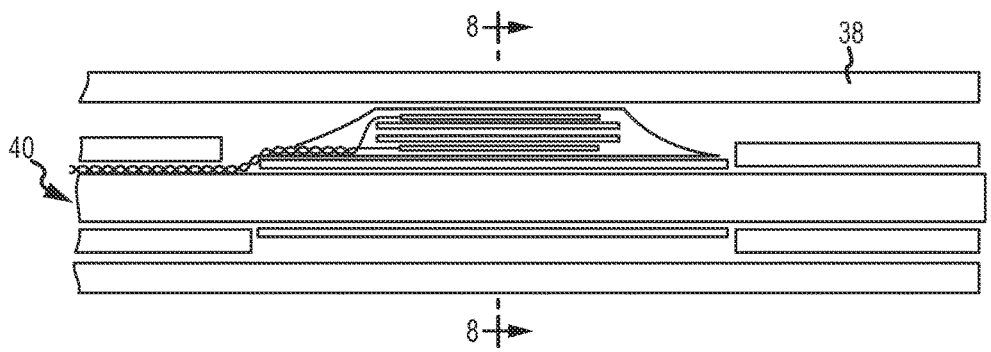

As shown in FIG. 5, the rest of first shaft layer 22 can then be placed on mandrel 16—i.e., segments $22_2$ and $22_3$ can be placed proximally and distally of segment $22_1$. Wiring 36 can be disposed radially-inwardly of first shaft layer segment $22_2$—i.e., the segment axially proximal of sensor 26—so that wiring 36 can be disposed in the central lumen of the finished device. Segment $22_2$ is shown as asymmetrical across axis "A" to better show wiring 36, but segment $22_2$ can be applied as a substantially symmetrical segment, such as a tube. Segments $22_1$, $22_2$, $22_3$ can have axial lengths and radial thicknesses that are different from each other, or they can have the same relative lengths and thicknesses. As noted hereinabove, the axial length of segment $22_1$ can be selected relative to the size of sensor 26 or sensor assembly 24. The axial lengths of segments $22_2$ and $22_3$ can be selected according to the desired placement of one or more sensors 26 in device 10. Segments $22_2$ and $22_3$ can have thicknesses substantially equal to each other, which can be greater than the thickness of segment $22_1$.

Figure 7:
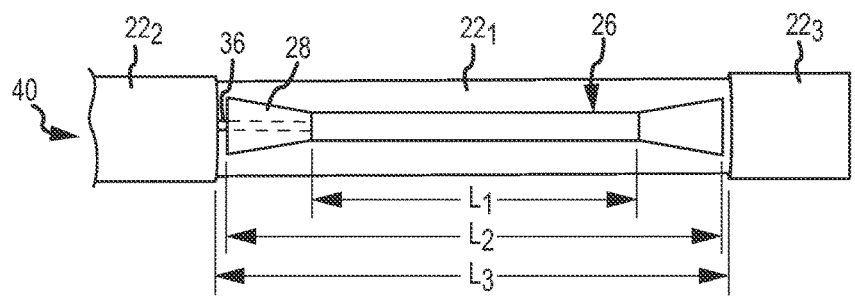
FIG. 7 is a top view of the distal tip assembly of the first embodiment at the stage of fabrication shown in FIG. 5.

FIG. 7 is a top view of sensor assembly 26 disposed on—i.e., laying on—first layer segment $22_1$ at the same stage of construction as FIG. 5. Sensor core 30 has an axial length $L_1$, which can be less than axial length $L_2$ of sleeve 28, which can be substantially equal to length $L_3$ of first shaft segment $22_1$. Sleeve axial length $L_2$ is shown smaller than first shaft segment length $L_3$ for visual clarity, though $L_2$ can be substantially equal to $L_3$ or can even be larger than $L_3$.

A second shaft layer 38 can then be placed over the entire distal tip assembly 40, as shown in FIG. 6, including first shaft layer 22 and sensor assembly 24. Second shaft layer 38 can be the same material as the first shaft layer (i.e., a melt-processing polymer such as PEBAX®). Second shaft layer 38 can have the same radial thickness as thicker first shaft layers $22_2$ and $22_3$.

After second shaft layer 38 is added to the assembly, the assembly can be subjected to a reflow lamination process, which involves heating the assembly until first shaft layer 22 and second shaft layer 38 flow and redistribute around the circumference of the assembly, bonding with an outer surface of sleeve 28 to embed sleeve 28. In one embodiment, the reflow process includes heating the assembly to about 450° F. (e.g., in an oven-like appliance), though the reflow temperature can vary for other embodiments. The assembly can then be cooled, after which first shaft layer 22 and second shaft layer 38 form a unitary shaft 42. Shaft 42 can have a proximal end portion and distal end portion coincident with mandrel proximal end portion 20 and mandrel distal end portion 18, respectively.

Figure 8:
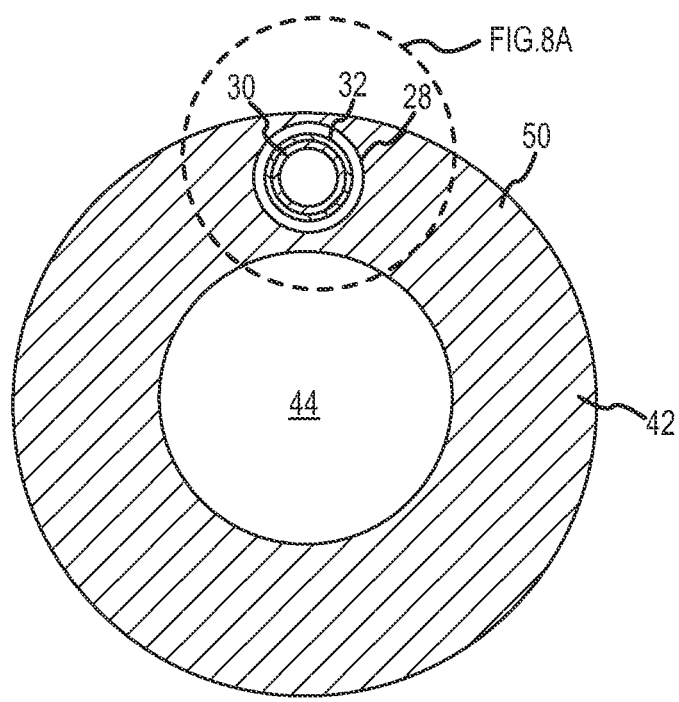
FIGS. 8 and 8A are cross-sectional views of the distal tip assembly of the first embodiment.
Figure 8A:
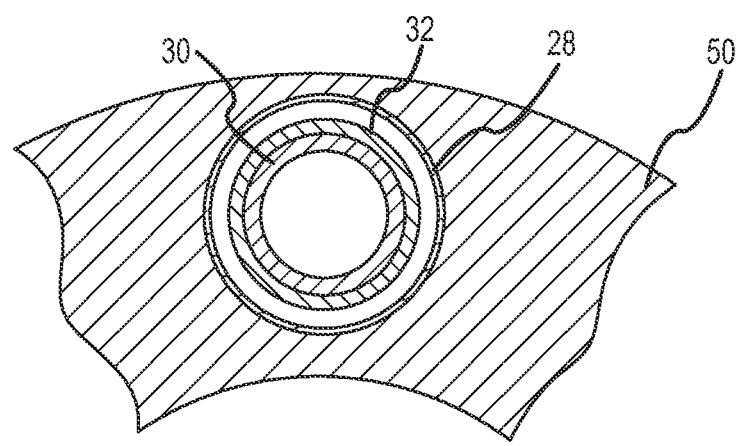

FIGS. 8 and 8A illustrate distal tip assembly 40 after the reflow lamination process and after the removal of mandrel 16. Shaft 42 has a central lumen 44 extending along axis "A" (formerly the central axis of mandrel 16) between the proximal end portion of shaft 42 and the distal end portion of shaft 42. Protection sleeve 28 can be embedded within a wall 50 of shaft 42, but the outer diameter (O.D.) of sensor 26 can be separated from, or at least not bonded to, the inner diameter (I.D.) of sleeve 28, so sensor 26 can remain free to move (e.g., shift) relative to sleeve 28. It should be understood that although a relatively large gap is shown between the I.D. of sleeve 28 and the O.D. of sensor 26 (i.e., outside surface of coil 32), sleeve 28 can be relatively tight to coil 32 and core 30 after the reflow lamination process, while still allowing coil 32 and core 30 to shift relative to sleeve 28 and wall 50.

Figure 9:
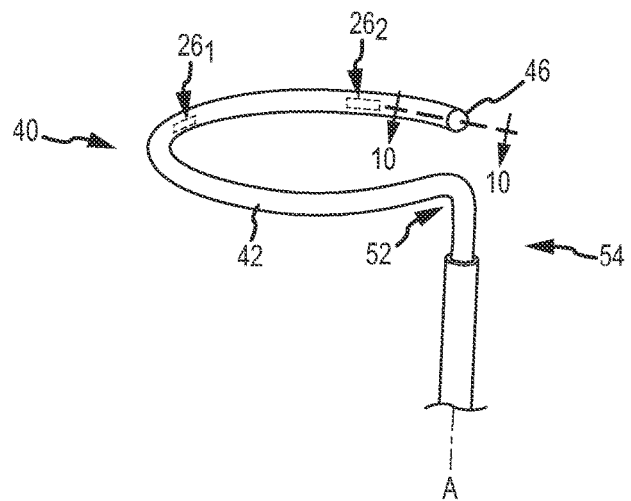
FIG. 9 is an isometric view of a distal end portion of the first embodiment.

FIG. 9 is an isometric view of a distal end portion 54 of device 10 after the addition of a tip electrode 46 and a shape wire 48 (best shown in FIG. 10) to distal tip assembly 40. Shape wire 48 can extend through distal end portion 54 and further proximally through device 10 and can be configured to establish a pre-defined shape for distal end portion 54. In device 10, shape wire 48 establishes a lariat shape along a plane substantially perpendicular to device axis "A". Shape wire 48 can be a super-elastic or shape memory metallic alloy, such as Nitinol, or another super-elastic or shape memory material. In a super-elastic embodiment, shape wire 48 can be pre-formed to a desired shape for a particular portion of device 10. Device 10 can be straightened or otherwise deformed through the application of force, then return to its pre-formed shape by virtue of the super-elasticity of shape wire 48 after the removal of the deforming force. For example, distal tip assembly 40 can be straightened by manual force and inserted to the heart through an introducer. The introducer can maintain the deforming (straightening) force as device 10 is advanced through the introducer. As distal tip assembly 40 emerges from the introducer into the heart, it would return to the pre-formed lariat shape of shape wire 48. In a shape memory embodiment, shape wire 48 can have a "naturally" straight shape but form a pre-determined shape (such as the lariat shape of distal tip assembly 40) upon exposure to an increased temperature (such as in the human body). Although shape wire 48 is shown with a distal portion that forms a lariat shape, shape wire 48 can be used to form a variety of shapes within the scope and spirit of the present invention. Additionally, shape wire 48 can also be configured as a pull wire, such that the application of force at the proximal end of device 10 (such as pulling on wire 48) can alter the shape of distal tip assembly 40. For example, pulling on shape wire 48 can decrease the radius of the lariat shape.

One method of adding tip electrode 46 and shape wire 48 to device 10 is to pre-couple shape wire 48 with tip electrode 46, then thread shape wire 48 through lumen 44. In doing so, shaft 42 and one or more position sensors—shown in outline form as $26_1$ and $26_2$ although within wall 50 of shaft 42—must be guided over the curvature of shape wire 48. Shape wire 48 can include one or more sharp bends, such as bend 52, that can place a large amount of stress on shaft 42 and any components disposed within wall 50. However, because sensors $26_1$, $26_2$ are within sleeves 28 instead of embedded directly in wall 50, sensors $26_1$, $26_2$ can shift and move relative to the portion of wall 50 surrounding each sensor 26, thereby reducing or eliminating the direct mechanical stress transmitted through wall 50 that would otherwise be imparted to each sensor 26. In other words, each sensor 26 is tethered within wall 50, rather than rigidly embedded in wall 50. Thus, each sensor 26 can be guided over bend 52 and other stress-inducing portions of shape wire 48 without breaking Even though each sensor 26 can shift relative to the portion of wall 50 surrounding the sensor 26, sleeve 28 and wiring 36 ensure that each sensor remains in a predictable location for position sensing and navigation purposes.

Figure 10:
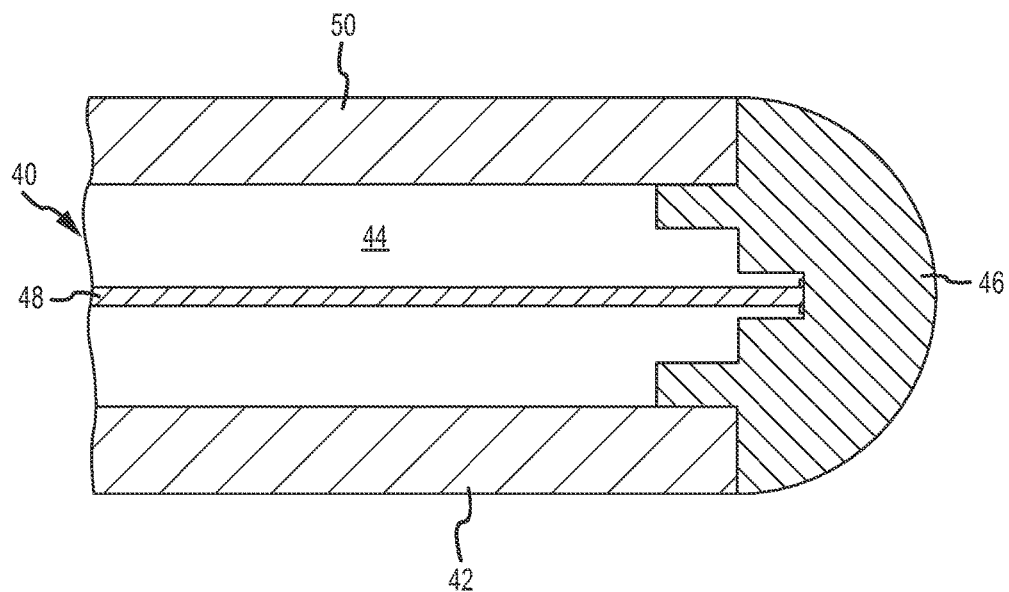
FIG. 10 is a cross-sectional view of the extreme distal end of the first embodiment, taken substantially along line 10-10 in FIG. 9.

FIG. 10 is a cross-sectional view of the extreme distal end of distal tip assembly 40, taken substantially along line 10-10 in FIG. 9. Tip electrode 42 can be coupled to the extreme distal tip of shaft 42 through methods known in the art. Shape wire 48 can be coupled to an inner surface of tip electrode 46 through a metallurgical process such as soldering, brazing, welding, or another process known in the art. Shape wire 48 can have a circular radial cross-section, or can have a different cross-section as needed for specific applications. Although tip assembly 40 has only one shape wire 48, more than one shape wire 48 can be used. Each wire used can serve as either a shape wire having a pre-determined shape, as a pull wire, or as both. For example, device 10 can incorporate only a single shape/pull wire 48 as shown in FIG. 10, or can have multiple shape and pull wires. A more detailed explanation of shape wires and of joining a shape wire to a tip electrode can be found in commonly-owned U.S. Pat. No. 7,706,891, entitled "Catheter Employing Shape Memory Alloy Shaping Wire or Pull Wire and Method of Its Manufacture," hereby incorporated by reference in its entirety.

Figure 11:
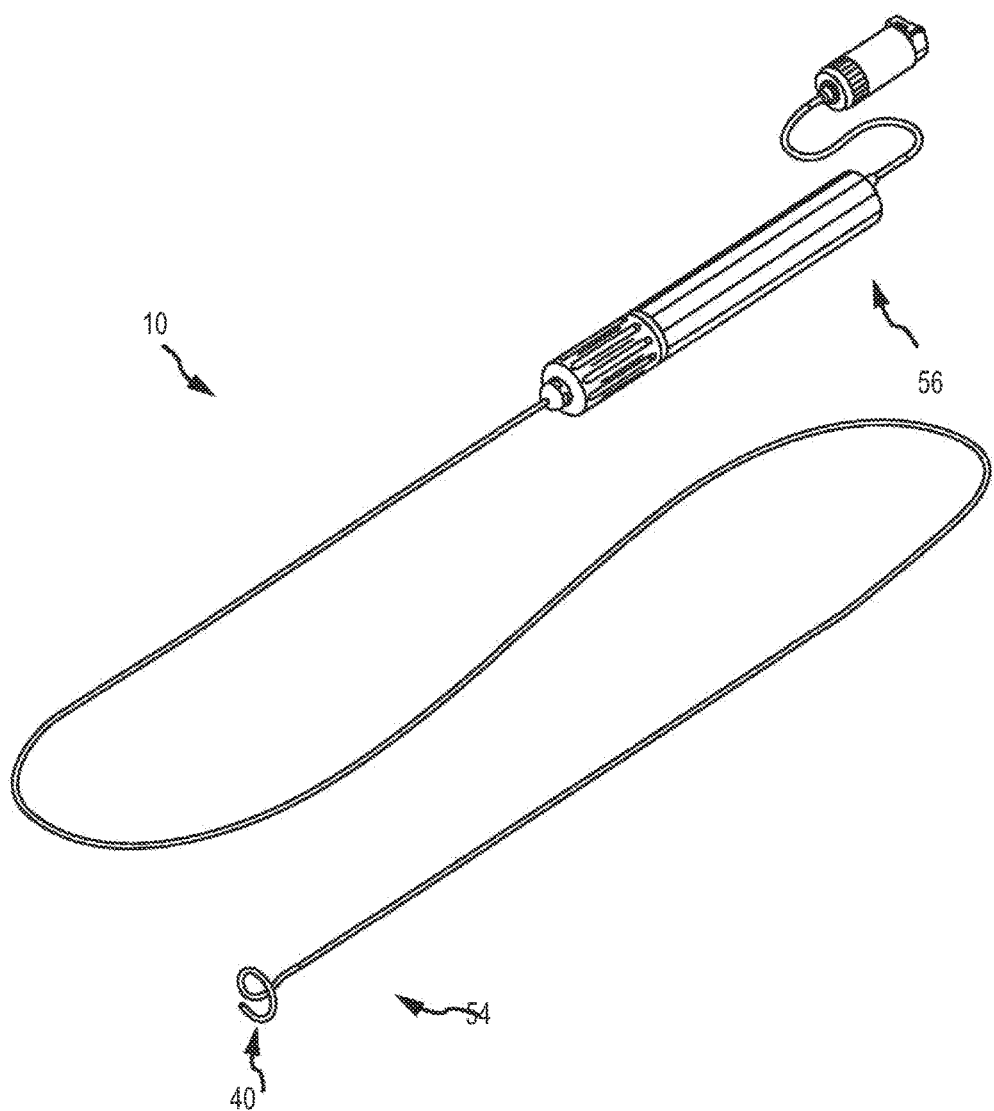
FIG. 11 is an isometric view of the first embodiment, including a proximal end portion.

FIG. 11 is an isometric view of elongate medical device 10 having completed distal tip assembly 40. Distal end portion 54 has a lariat shape according to the curvature of shape wire 48. After coupling tip electrode 46 and shape wire 48 with assembly 40, assembly 40 can be completed by various other steps known in the art or by adding other features known in the art, such as additional wiring, layers, or one or more additional electrodes. For example, in addition to tip electrode 46, distal end portion 54 can include 9 band electrodes ("decapolar" catheter) or 19 band electrodes ("duo-decapolar" catheter). A proximal end portion 56 of device 10 can provide the ability to connect device 10 to navigation and mapping systems and power sources, as well as the ability to manipulate distal end portion 54 of device 10.

In an exemplary embodiment of distal tip assembly 40, shaft 42 can have a desired inner diameter (ID) of about 0.048 inches and a desired outer diameter (OD) of about 0.065 inches. In such an exemplary embodiment, first shaft layer segment $22_1$ can have an ID of about 0.048 inches and an OD of about 0.050 inches. Sensor assembly 24 can have an OD of about 0.013 inches. First shaft layer segments $22_2$ and $22_3$ can each have an ID of about 0.048 inches and an OD of about 0.052 inches. Second shaft layer 38 can have an ID of about 0.058 inches and an OD of about 0.062 inches. First shaft layer 22 and second shaft layer 38 can both be PEBAX® material with a 55D durometer. After reflow lamination, the exemplary embodiment can have the desired ID, desired OD, and have sensor 26 tethered within wall 50.

Manufacturing distal tip assembly 40, distal end portion 54, and device 10 according to the methods described in conjunction with FIGS. 2-11 presents many advantages. Electromagnetic position sensor 26 is disposed within sleeve 28 such that sensor 26 can shift relative to sleeve 28. Accordingly, sensor 26 is not subjected to all of the stress placed on wall 50 as shaft 42 is threaded over shape wire 48. But because outer sleeve 28—which contains sensor 26—is at least in part embedded in or otherwise substantially fixed to wall 50, the shifting and movement of sensor 26 relative to wall 50 can remain within a certain tolerance such that sensor 26 can still reliably be used for position sensing and device navigation. As a result, one or more position sensors 26 can be incorporated into a medical device with a shape wire 48 of many different shapes, such as a lariat shape in its distal end portion.

It should be understood that the embodiments of device 10, distal tip assembly 40, and distal end portion 54 are exemplary in nature. Variations could be made and still fall within the spirit and scope of the claimed invention. For example, distal tip assembly 40 can have one, two, three, or more position sensors 26 or position sensor assemblies 24. Multiple sensors 26 or sensor assemblies 24 can require more first shaft layer segments $22_1, \ldots, 22_n$ than specified in the embodiments herein. The lengths and thicknesses of shaft layers 22, 38 can be configured for specific devices and applications. Similarly, the durometer of shaft layers 22, 38 can be tailored to a specific application and the durometer of shaft 42 (and/or the entire shaft of the finished device) can vary over its length. Lumen 44 can be larger or smaller than the embodiments described herein depending on the required dimensions and features of a particular device. Other modifications and additions known in the art can also be possible.

Figure 12:
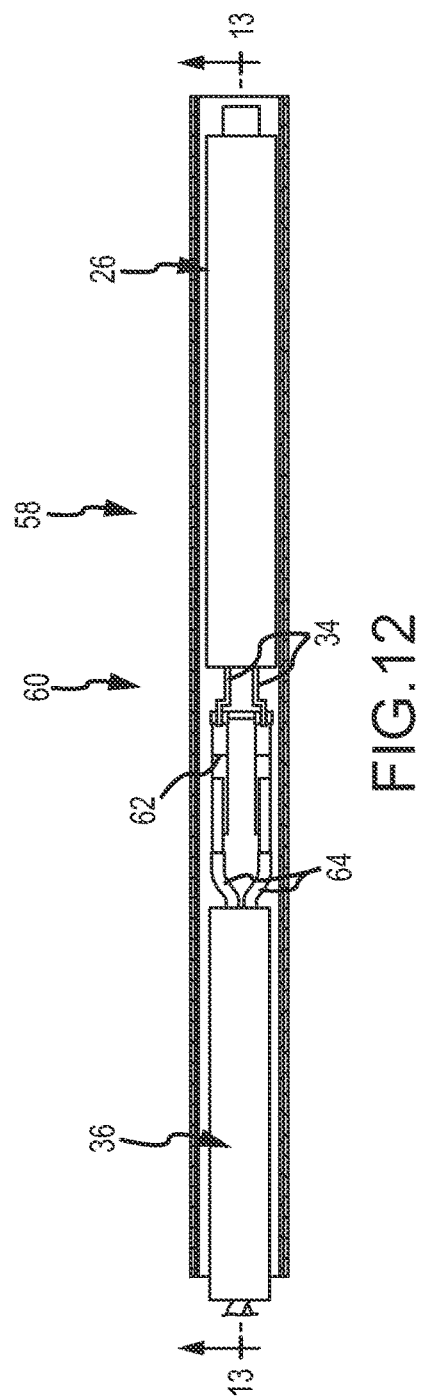
FIG. 12 is a side view of a distal portion of another embodiment of an elongate medical device, having a flex circuit, with a portion of the outer jacket cut away.

FIG. 12 is a side view of a distal end portion 58 of a second embodiment 60 of an elongate medical device, with a portion of the outer jacket cut away to show interior components. Device 60 includes a first embodiment of a flex circuit 62 for connecting wiring 36 to sensor 26. Wiring 36 can have leads 64, consisting of a first free end and a second free end. Sensor leads 34 can also consist of a first free end and a second free end. Flex circuit 62 can electrically connect the first free end of wiring leads 64 to the first free end of sensor leads 34 to form a first electrical path and the second free end of wiring leads 64 to the second free end of sensor leads 34 to form a second electrical path while electrically separating the first and second electrical paths. Circuit 62 can have a size and shape appropriate for the needed application. Flex circuit 62 can abut sensor 26 on one axial end (the distal end of circuit 62 in device 60) and can abut wiring 36 on the other axial end (the proximal end of circuit 62 in device 60). If wiring 36 has a shielding, housing, or other outer layer, as shown, flex circuit 62 can extend up to the outer layer or can extend partially into or adjacent to the outer layer.

Figure 13:
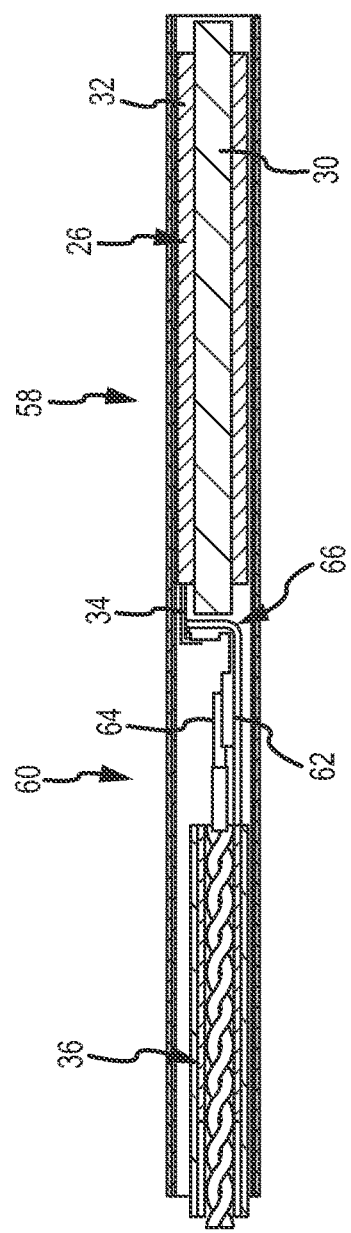
FIG. 13 is a cross-sectional view of an embodiment of an elongate medical device, taken substantially along line 13-13 in FIG. 12.

FIG. 13 is a cross-sectional view of catheter 60, taken substantially along line 13-13 in FIG. 12. As in device 10, sensor 26 in catheter 60 can be an electromagnetic coil sensor, including a tubular core 30 and a coil 32 wrapped around core 30. Flex circuit 62 can have a bend 66 to create contact surfaces in separate planes. A contact surface can have a greater radial dimension than axial dimension ("radial contact pad"), or a greater axial dimension than radial dimension ("axial contact pad"). Wiring leads 64 and sensor leads 34 can be coupled to circuit 62 through soldering or another electrically-conductive coupling method.

FIGS. 14-17 are various isometric and plan views of flex circuit 62. Circuit 62 can include an electrically-insulative substrate 78 and two sets of contact pads 68, 70 electrically connected by thin, electrically-conductive traces 72. Contact pads 68, 70 can be made of an electrically-conductive material that can easily be coupled with wiring leads 64 and sensor leads 34, such as solder. Traces 72 can be an electrically-conductive material, such as brass. Contact pads 68 can be axial contact pads and can be provided at the proximal end of circuit 62 for connection with wiring leads 64. Contact pads 70 can be radial contact pads and can be provided at the distal end of circuit 62 for connection with sensor leads 34. Substrate 78 can also have an axial extension portion 74 extending axially from contact pads 68. Axial extension portion 74 can have a length similar or substantially equal to the length of associated leads, such as wiring leads 64. In an exemplary embodiment, axial length $L_4$ of flex circuit 62 can be about 0.038 inches, length $L_5$ of the contact portion (i.e., the portion of circuit 62 including contact pads 68, 70, and traces 72) of circuit 72 can be about 0.020 inches, and length $L_6$ of axial extension portion 74 can be about 0.018 inches.

Figure 18:
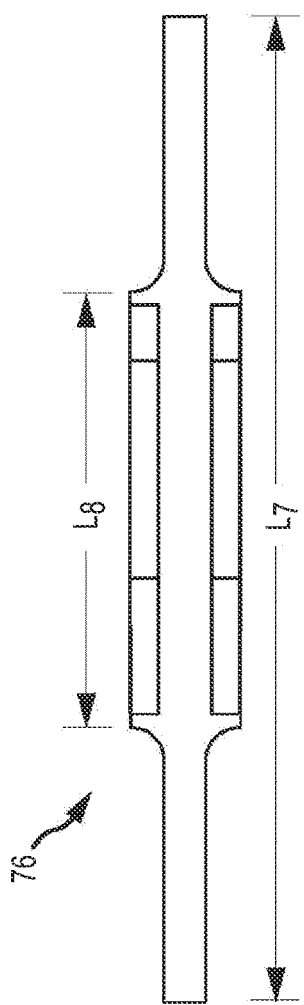
FIGS. 18-19 are plan views of an embodiment of a flex circuit according to the instant disclosure.
Figure 19:
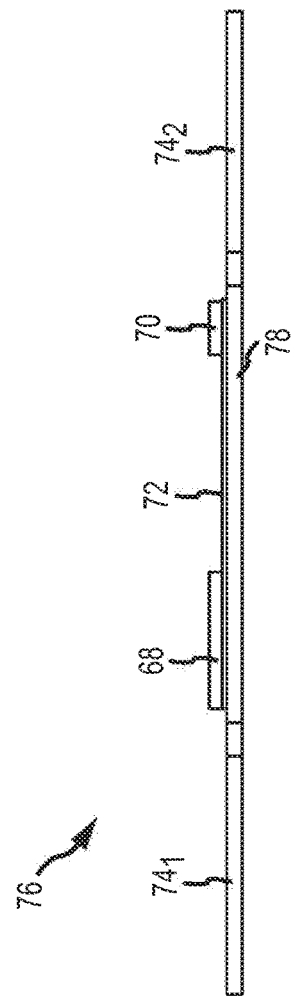

FIGS. 18-19 are plan views of a second embodiment 76 of a flex circuit. Circuit 76 performs the same functions as circuit 62 as described above, except where otherwise noted, but is slightly different in form. Circuit 76 can include substrate 78 and two pairs or sets of contact pads 68, 70, both of which are axial contact pads. Contact pads 68, 70 can be joined by axially-extending electrically-conductive traces 72. Substrate 78 can also include two axial extension portions 74$_1$, 74$_2$ (one at the proximal end of circuit 76 and one at the distal end). Circuit 76 can be used instead of circuit 62 when two axial extension portions are desired, or when two sets of axial contact pads are desired.

In an embodiment of circuit 76, axial length $L_7$ of circuit 76 can be about 0.072 inches. Length $L_8$ of the contact portion of circuit 76 can be about 0.032 inches. Contact pads 68 can have an axial length of about 0.010 inches, and contact pads 70 an axial length of about 0.004 inches. Traces 72 can have an axial length of about 0.0158 inches. Contact pads 68, 70, and traces 72 can each have a width of about 0.002 inches.

Although only shown specifically with device 60, a flex circuit such as flex circuit 62 or flex circuit 76 can find use with any device for which electrical coupling between two sets of leads is desirable. For example, flex circuit 62 or 76 can be used in conjunction with elongate medical device 10 as an interface to couple sensor 26 with wiring 36.

Although numerous embodiments of this invention have been described above with a certain degree of particularity, those skilled in the art could make numerous alterations to the disclosed embodiments without departing from the spirit or scope of this invention. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure can be made without departing from the spirit of the invention as defined in the appended claims.

What is claimed is:

1. A method of fabricating a distal tip assembly for an elongate medical device having an axis, comprising:
    providing a first shaft layer;
    placing, at a distal end portion of said elongate medical device, a position sensor assembly on said first shaft layer, said position sensor assembly comprising a tubular core, an electrically-conductive coil wound on said core, and an outer sleeve surrounding said core and said coil;
    applying a second shaft layer radially-outwardly of said position sensor assembly and said first shaft layer; and
    subjecting said tip assembly to a reflow lamination process, wherein said first shaft layer and said second shaft layer bond to an outer surface of said sleeve, and said coil and said core can shift within said sleeve.

2. The method of claim 1, further comprising:
    coupling said coil to one or more wires; and
    extending said one or more wires axially toward a proximal end from said position sensor assembly.

3. The method of claim 1, further comprising:
    coupling a tip electrode to an extreme distal end of said distal end portion;
    placing a shape wire radially-inwardly of said first shaft layer; and
    coupling said shape wire to said tip electrode.

4. The method of claim 1, wherein said first shaft layer and said second shaft layer comprise PEBAX material.

5. The method of claim 1, wherein said outer sleeve comprises expanded polytetrafluoroethylene (ePTFE).

6. The method of claim 3, wherein said shape wire comprises Nitinol.

7. The method of claim 1, wherein an axial length of said sleeve is greater than an axial length of said core.

8. A method of fabricating an elongate medical device having an axis, comprising:
    placing a sensor assembly on a first portion of a first shaft layer, wherein said first portion is proximate a second portion and a third portion of said first shaft layer;
    applying a second shaft layer radially-outwardly of said sensor assembly and said first portion, said second portion, and said third portion of said first shaft layer; and
    bonding said second portion and said third portion of said first shaft layer and said second shaft layer, wherein said sensor assembly can shift relative to said second shaft layer.

9. The method of claim 8, further comprising:
    coupling said sensor assembly to one or more electrical wires; and
    extending said one or more electrical wires proximally from said sensor.

10. The method of claim 8, further comprising:
    coupling a tip electrode to an extreme distal end of a distal end portion;
    placing a shape wire radially-inwardly of said first shaft layer; and
    coupling said shape wire to said tip electrode.

11. The method of claim 8, wherein said first shaft layer and said second shaft layer comprise PEBAX material.

12. The method of claim 8, wherein said sensor assembly comprises a sensor comprising a tubular core and an electrically-conductive coil wound on said core, the method further comprising:
    placing said sensor in an outer sleeve surrounding said core and said coil.

13. The method of claim 8, wherein said sensor assembly comprises an outer sleeve, wherein applying said second shaft layer radially-outwardly of said sensor assembly and said first shaft layer comprises applying said second shaft layer radially-outwardly of said outer sleeve.

14. The method of claim 13, wherein said outer sleeve comprises expanded polytetrafluoroethylene (ePTFE).

15. The method of claim 13, wherein bonding said first shaft layer and said second shaft layer to an outer surface of said sensor assembly encapsulates said outer sleeve.

* * * * *